(12) United States Patent
Reiderman (10) Patent No.: US 7,423,426 B2
(45) Date of Patent: Sep. 9, 2008

(54) SELECTIVE EXCITATION IN EARTH'S MAGNETIC FIELD NUCLEAR MAGNETIC RESONANCE WELL LOGGING TOOL

(75) Inventor: Arcady Reiderman, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 210 days.

(21) Appl. No.: 11/743,863

(22) Filed: May 3, 2007

(65) Prior Publication Data

US 2008/0007260 A1    Jan. 10, 2008

Related U.S. Application Data (63) Continuation-in-part of application No. 11/494,043, filed on Jul. 27, 2006, which is a continuation-in-part of application No. 11/037,488, filed on Jan. 18, 2005.

(60) Provisional application No. 60/542,932, filed on Feb. 9, 2004.

(51) Int. Cl.
*G01V 3/00* (2006.01)
(52) U.S. Cl. .......................... 324/303; 324/307
(58) Field of Classification Search ............... 324/303, 324/307
See application file for complete search history.

(56) References Cited

U.S. PATENT DOCUMENTS

| | | | |
|---|---|---|---|
| 3,538,429 A | 11/1970 | Baker, Jr. |
| 3,731,752 A | 5/1973 | Schad |
| 4,035,718 A | 7/1977 | Chandler |
| 4,489,276 A | 12/1984 | Yu |
| 4,536,714 A | 8/1985 | Clark |
| 4,538,109 A | 8/1985 | Clark |
| 4,574,242 A | 3/1986 | Clark et al. |
| 4,584,586 A | 4/1986 | Kocsi |
| 4,603,297 A | 7/1986 | Safinya |
| 4,717,878 A | 1/1988 | Taicher et al. |
| RE32,913 E | 4/1989 | Clark |
| 5,055,787 A | 10/1991 | Kleinberg et al. |
| 5,600,330 A | 2/1997 | Blood |
| 5,710,511 A | 1/1998 | Taicher et al. |
| 5,955,884 A | 9/1999 | Payton et al. |
| 6,002,317 A | 12/1999 | Pignataro |
| 6,166,543 A | 12/2000 | Sezginer et al. |
| 6,229,422 B1 | 5/2001 | Pignataro |
| 6,348,792 B1 | 2/2002 | Beard et al. |
| 6,366,086 B1 | 4/2002 | Sen |
| 6,452,388 B1 | 9/2002 | Reiderman et al. |
| 6,459,262 B1 | 10/2002 | Wisler et al. |
| 6,541,979 B2 | 4/2003 | Omeragic |
| 6,556,015 B1 | 4/2003 | Omeragic et al. |
| 6,580,273 B2 | 6/2003 | Reiderman et al. |
| 6,584,408 B2 | 6/2003 | Omeragic |
| 6,690,170 B2 | 2/2004 | Homan et al. |
| 6,727,705 B2 | 4/2004 | Frey et al. |

(Continued)

*Primary Examiner*—Brij B. Shrivastav
*Assistant Examiner*—Megann E Vaughn
(74) *Attorney, Agent, or Firm*—Cantor Colburn LLP (57) ABSTRACT

A downhole nuclear magnetic resonance method for measuring a property of a formation, the method includes applying a polarizing magnetic field to the formation, the field including a spatial distribution of magnitude; selecting an investigation region of the formation; decaying the polarizing magnetic field according to a decay shape to provide for substantially exciting only nuclei in the investigation region; and measuring signals induced by precession of the nuclei in the investigation region.

23 Claims, 12 Drawing Sheets

U.S. PATENT DOCUMENTS

| | | |
|---|---|---|
| 6,819,110 B2 | 11/2004 | Omeragic et al. |
| 6,819,112 B2 | 11/2004 | Gianzero et al. |
| 6,891,376 B2 | 5/2005 | Hanstein et al. |
| 6,930,652 B2 | 8/2005 | Smith et al. |
| 6,933,726 B2 | 8/2005 | Chen et al. |
| 6,937,021 B2 | 8/2005 | Rosthal |
| 7,023,212 B2 | 4/2006 | Chen et al. |
| 7,138,897 B2 | 11/2006 | Ninerbo et al. |
| 7,193,420 B2 | 3/2007 | Chen et al. |
| 7,202,670 B2 | 4/2007 | Omeragic et al. |
| 2004/0183538 A1 | 9/2004 | Hanstein et al. |
| 2004/0263414 A1 | 12/2004 | Chen et al. |
| 2005/0116718 A1 | 6/2005 | Chen et al. |
| 2005/0140373 A1 | 6/2005 | Li et al. |
| 2005/0189945 A1 | 9/2005 | Reiderman |
| 2006/0192561 A1 | 8/2006 | Chesser et al. |
| 2006/0192562 A1 | 8/2006 | Davydychev et al. |
| 2006/0253255 A1 | 11/2006 | Omeragic et al. |

SELECTIVE EXCITATION IN EARTH'S MAGNETIC FIELD NUCLEAR MAGNETIC RESONANCE WELL LOGGING TOOL

CROSS-REFERENCES TO RELATED APPLICATIONS

This application is filed under 37 CFR 1.53(b) as a continuation-in-part of and claims priority under 35 U.S.C. 120 to U.S. patent application Ser. No. 11/494,043 filed on Jul. 27, 2006, which in turn claims priority to U.S. patent application Ser. No. 11/037,488 filed on Jan. 18, 2005, which in turn claims priority to U.S. Provisional Patent Application No. 60/542,932 filed on Feb. 9, 2004, these applications being incorporated by reference in their entirety.

BACKGROUND OF THE INVENTION

1. Field of the Invention

This invention relates to the field of measuring nuclear magnetic resonance (NMR) properties of an earth formation.

2. Description of the Related Art

Geologic formations below the surface of the earth may contain reservoirs of oil and gas. Measuring properties of the geologic formations provides information that can locate the reservoirs of oil and gas. Typically, the oil and gas are retrieved by drilling boreholes into the subsurface of the earth. The boreholes also provide access to take measurements of the geologic formations.

Well logging is a technique used to take measurements of the geologic formations from the boreholes. A "logging instrument" (also referred to as a "logging tool") is lowered on the end of a wireline into the borehole. The logging instrument sends data via the wireline to the surface for recording. One type of measurement involves measuring nuclear magnetic resonance (NMR) properties from the geologic formations.

A new generation of NMR logging instruments based on using permanent magnets was introduced into practice about a decade ago (see for example U.S. Pat. No. 4,717,878 issued to Taicher et al., U.S. Pat. No. 5,055,787 issued to Kleinberg et al., and U.S. Pat. No. 6,452,388 issued to Reiderman, et al.). The new generation of NMR logging instruments has demonstrated obvious advantages over the old technologies (earth's magnetic field NMR logging) such as high resolution in acquiring NMR relaxation spectra, capability of diffusion measurements, as well as a defined volume of investigation with no effect of protons in the bore fluid on acquired NMR data.

It was recognized though that a high rate of decreasing static and radio frequency magnetic fields with distance from the NMR sensor results in a relatively small and shallow region of investigation. Consequently, an acceptable signal-to-noise ratio (SNR) can be achieved only at depths of investigation in a range of about one to four inches (typically corresponds to an invasion zone). Even in this range, the SNR is often not sufficient to allow for a desired logging speed.

Drawbacks of new NMR tools stimulated interest toward alternative designs including ones based on a modified early concept of an earth's magnetic field NMR logging tool. A typical earth's magnetic field NMR tool creates a static magnetic field to polarize nuclei of elements present in an earth formation. The static magnetic field is turned off to allow free or driven precession of the polarized nuclei about the earth's magnetic field. Signals generated by the free precession of nuclear spin magnetic moments are detected and correlated to elements in the earth formation. U.S. Pat. No. 3,538,429 issued to John H. Baker and U.S. Pat. No. 4,035,718 issued to Richard N. Chandler give examples of a technique that uses an abrupt (non-adiabatic) turning off of the static magnetic field and detecting signals generated by free precession of nuclear spin magnetic moments. U.S. Pat. No. 6,366,086 issued to Pabitra N. Sen addresses an issue of an undesirable signal acquired from borehole fluid. Drawbacks of techniques of this type are a poorly defined excitation region as well as a relatively low SNR due to power-consumption-limited intensity of the static magnetic field used to polarize the nuclei.

None of the methods and apparatus of prior art have been able to facilitate deep (on an order of one meter) NMR measurements. Facilitating the deep NMR measurements typically requires (1) generation of a large magnetic dipole as a source of the static magnetic field with a capability of switching the static magnetic field "off" in microseconds and (2) suppression of strong NMR signals emanating from shallow regions close to the borehole.

What are needed are a method and apparatus to produce the static magnetic field with the switching capability and to substantially eliminate the strong NMR signals emanating from shallow regions close to the borehole.

BRIEF SUMMARY OF THE INVENTION

The shortcomings of the prior art are overcome and additional advantages are provided through a downhole nuclear magnetic resonance method for measuring a property of a formation, the method includes applying a polarizing magnetic field to the formation, the field including a spatial distribution of magnitude; selecting an investigation region of the formation; decaying the polarizing magnetic field according to a decay shape to provide for substantially exciting only nuclei in the investigation region; and measuring signals induced by precession of the nuclei in the earth's magnetic field in the investigation region.

Also disclosed is a method for selecting a decay shape for decaying a polarizing magnetic field, the method includes evaluating a shape of a plurality of polarizing magnetic fields; and selecting the shape that produces a maximum magnetization of nuclei as a function of magnetic field intensity.

Also disclosed is an instrument for measuring a property of a formation downhole, the instrument includes a source adapted for applying a polarizing magnetic field to the formation, the field comprising a magnitude such that nuclei in a shallow region of the formation exhibit a substantially adiabatic precession when the polarizing magnetic field is decayed, and the source adapted for decaying the field, to provide a maximum magnetization of nuclei in an investigation region beyond the shallow region.

Further disclosed is a method for producing an instrument for measuring a property of a formation downhole, the method includes selecting a source of a polarizing magnetic field; and coupling the source to a processor, the processor having instructions for decaying the field.

BRIEF DESCRIPTION OF THE DRAWINGS

Referring now to the drawings wherein like elements are numbered alike in the several Figures.

DETAILED DESCRIPTION OF THE INVENTION

Figure 1:
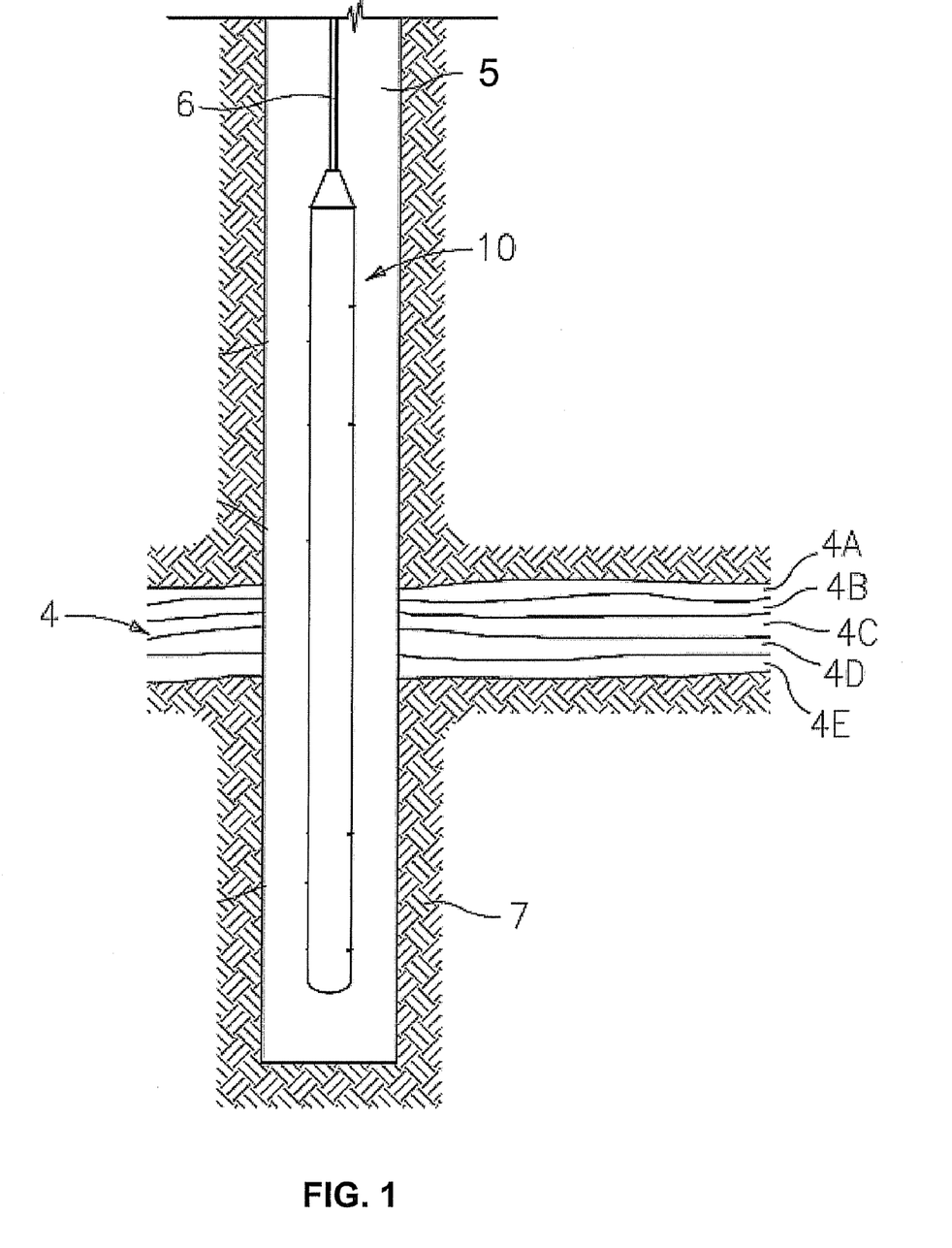
FIG. 1 illustrates an exemplary embodiment of a logging instrument in a borehole penetrating the earth.

Referring to FIG. 1, a well logging instrument 10 is shown disposed in a borehole 5. The borehole 5 is drilled through earth 7 and penetrates formation 4, which include various layers 4A-4E. The instrument 10 is typically lowered into and withdrawn from the borehole 5 by use of an armored electrical cable 6 or similar conveyance as is known in the art. For the teachings herein, the well logging instrument is designed to perform earth's magnetic field nuclear magnetic resonance (NMR) measurements.

In typical embodiments, the borehole 5 includes materials such as would be found in oil exploration, including a mixture of liquids including water, drilling fluid, mud, oil and formation fluids that are indigenous to the various formations. One skilled in the art will recognize that the various features as may be encountered in a subsurface environment may be referred to as "formations." Accordingly, it should be considered that while the term "formation" generally refers to geologic formations of interest, that the term "formations," as used herein, may, in some instances, include any geologic points of interest (such as a survey area).

As a matter of convention, one should note that the variables used herein appear throughout the disclosure. Accordingly, previously defined variables are generally not reintroduced. For convenience of referencing, the following representations are some of the definitions applied herein, or related to the teachings herein: γ represents a gyromagnetic ratio, $\vec{B}_P$ represents a polarizing magnetic field, $\vec{R}(T_1, T_2)$ represents a relaxation term that involves time constants $T_1$ and $T_2$ where $T_1$ is the time required for a magnetization vector to be restored to 63% of its original amplitude (referred to as "longitudinal relaxation time") and $T_2$ is the time required for the magnetization vector to drop to 37% of its original amplitude (referred to as "transverse relaxation time").

Figure 2:
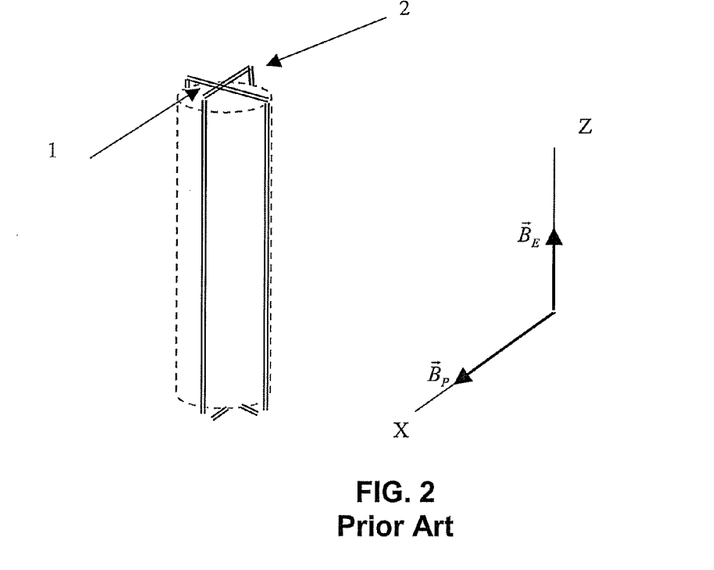
FIG. 2 illustrates a prior art example of implementation of an earth's magnetic field NMR method.
Figure 3:
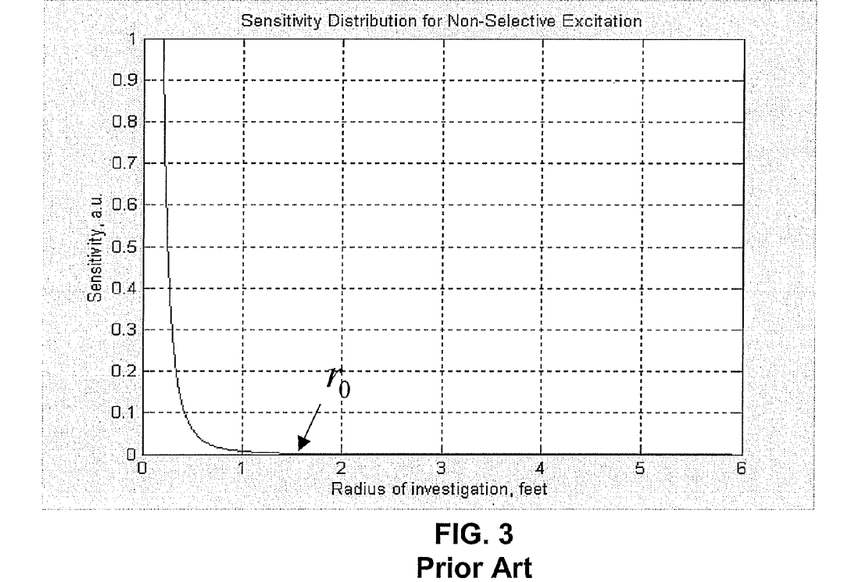
FIG. 3 illustrates a prior art example of a radial sensitivity distribution for an NMR signal.

FIG. 2 illustrates a prior art example of implementation of an earth's magnetic field NMR method. A transversal dipole source of a polarizing magnetic field $\vec{B}_P$ is a polarizing coil 1. The polarizing coil 1 polarizes nuclei in materials of the formation 4. The nuclei are polarized for a time period exceeding an expected longitudinal relaxation time of the nuclei. Upon sudden removal of the polarizing magnetic field, nuclear magnetization aligned in a direction of the polarizing magnetic field start precession around the earth's magnetic field $\vec{B}_E$ (in Z-axis direction) with frequency $\omega_E = \gamma \cdot \vec{B}_E$, known as the Larmor frequency. The precession results in inducing NMR signals in a receiver coil 2. The receiver coil 2 can be wound in the same plane as the polarizing coil 1 or in an orthogonal plane as shown in FIG. 2. Since both a polarizing coil 1 intensity and a receiver coil 2 sensitivity reduce rapidly with distance from the logging instrument 10, the NMR signals received by the receiver coil 2 will represent mostly properties of materials in a vicinity of the borehole 5 (also described as a shallow region). An example of a radial sensitivity distribution for the NMR signals is illustrated in FIG. 3. If a region of interest corresponds to $r > r_0$ where $r_0$ is much greater than a diameter of the borehole 5, then the NMR signals coming from the region of interest are almost negligible compared to the NMR signals coming the shallow regions. The process of applying and removing the polarizing magnetic field to cause the precession of nuclei is referred to as "excitation."

The teachings provide for suppressing the NMR signals from the shallow regions and exciting the nuclei in elements of the formations 4 at a selected distance from the well logging instrument 10. The suppressing of the NMR signals from the shallow regions and the excitation of nuclei in elements of the formations 4 at a selected distance is referred to as "selective excitation." Suppression of the NMR signal from the shallow regions is accomplished by insuring that magnetization changes of the nuclei in the shallow regions follow an adiabatic process. In the adiabatic process in the shallow regions, substantial precession of nuclei does not occur and, correspondingly, a Larmor frequency signal is not induced in the receiver coil 2. The selected distance, where the excitation of nuclei occurs, may be determined by selecting appropriate shape parameters for decay of the polarizing magnetic field. A method for accomplishing selective excitation is discussed in detail next.

Figure 4:
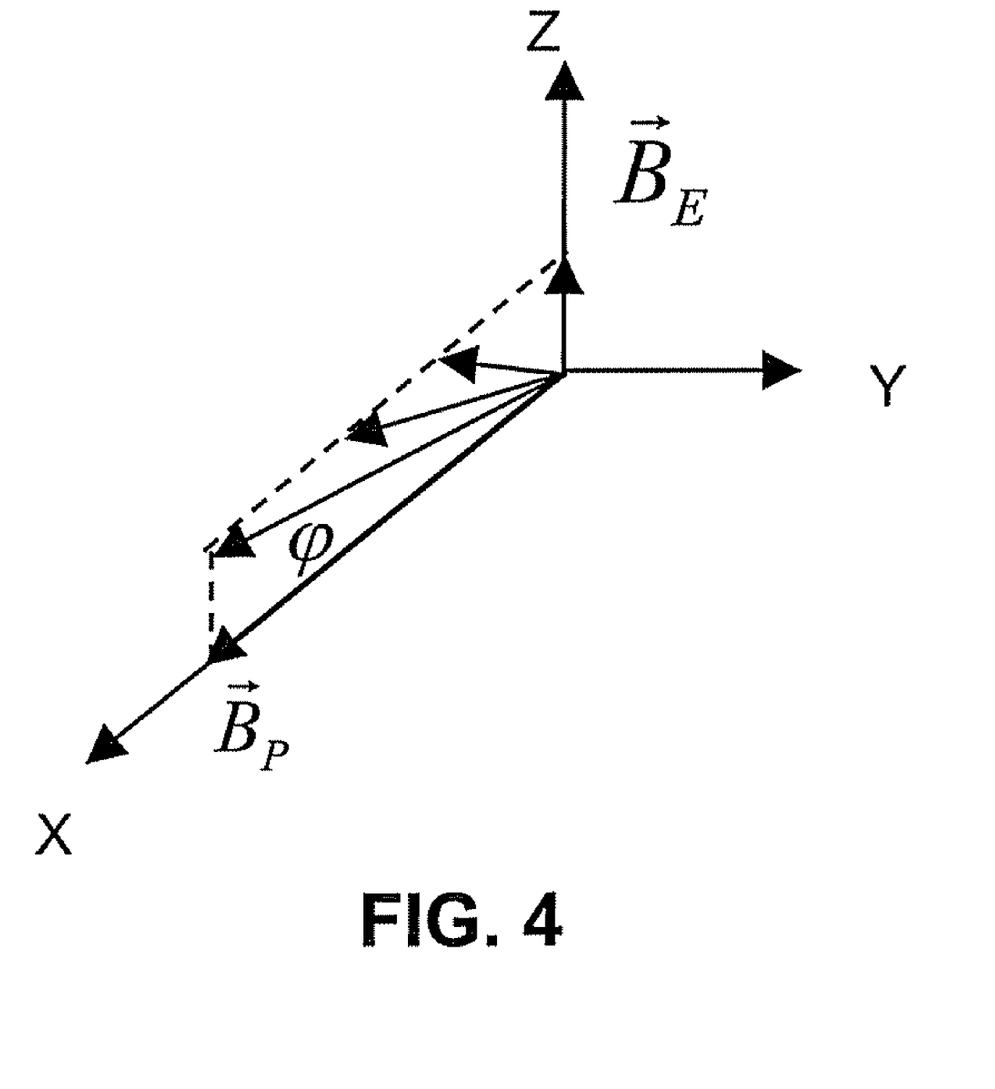
FIG. 4 illustrates variation of an angle φ of a total magnetic field with respect to an X-axis.

Magnetization changes can be described mathematically as follows. FIG. 4 illustrates variation of an angle φ of a total magnetic field $\vec{B} = \vec{B}_P + \vec{B}_E$ with respect to the X-axis. An angular frequency vector is defined as $$\vec{\Omega} = \frac{d\varphi}{dt} \cdot \vec{e}_Y,$$

where $\vec{e}_Y$ is a unity-pointing vector. Equation 1, known as a Bloch equation, can be used to describe magnetization changes in a coordinate system having the Z-axis aligned with an instantaneous direction of a magnetic field:

$$\frac{d\vec{M}}{dt} = \gamma \cdot \left[\vec{M} \times \left(\vec{B}_{\text{eff}} + \frac{\vec{\Omega}}{\gamma}\right)\right] + \vec{R}(T_1, T_2) \quad (1)$$

where $\vec{M}$ is nuclear magnetization that is initially equal to a magnitude $M_0$ (at time t=0) and directed along $\vec{B}_P$, $\vec{B}_{\text{eff}}$ is the effective magnetic field applied to material in the formation 4 undergoing the magnetization changes, $\vec{\Omega}$ is the angular frequency vector, $\vec{R}(T_1, T_2)$ is the relaxation term discussed above. For a qualitative discussion as below, the relaxation term can be neglected.

Following from equation (1) are two regimes of magnetization changes. In one regime, magnetization changes in an "adiabatic process." In an opposite regime, the magnetization changes in a "non-adiabatic process." For example, sudden removal of the polarizing magnetic field causes precession of a magnetization vector around a residual magnetic field such as the earth's (aligned in the Z-axis direction). A magnitude of a magnetization component in an X-Y plane is equal to $M_0$ (at time=0). Slow change of the polarizing magnetic field makes the magnetization follow the total magnetic field (the adiabatic process) with no significant component of magnetization perpendicular to an instantaneous direction of the total magnetic field. An "adiabacity factor" is a criterion separating the two regimes of magnetization changes. The adiabacity factor may be defined as:

$$\xi = \frac{|\vec{\Omega}|}{\gamma \cdot |\vec{B}|} \quad (2)$$

If $\xi \ll 1$, then no "excitation" of the nuclei occurs that results in a significant magnetization component perpendicular to the instantaneous direction of the total magnetic field. For $\xi \gg 1$, a full magnitude excitation of the nuclei occurs that results in a significant magnetization component perpendicular to the instantaneous direction of the total magnetic field.

Figure 5:
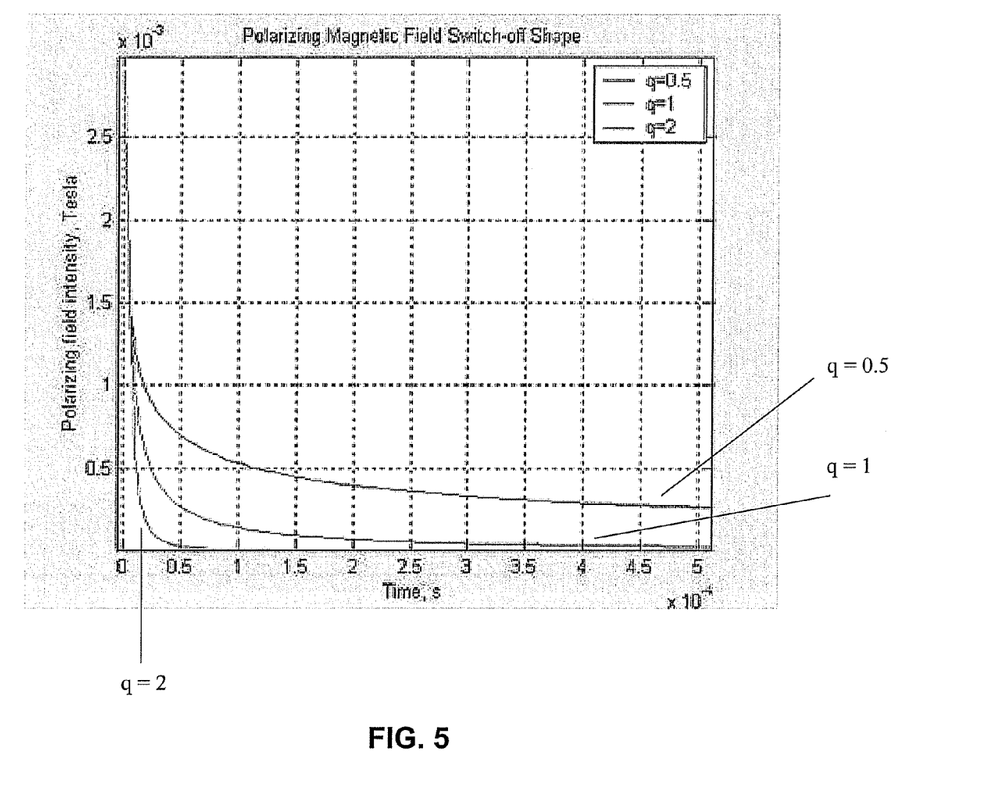
FIG. 5 illustrates an example of a decay shape when a polarizing magnetic field is switched off.

When the polarizing magnetic field is switched off, the polarizing magnetic field may have a distinctive decay shape, also referred to as a "switch-off" shape. An example of the switch-off shape for the polarizing magnetic field $B_P$ can be described by the equation $$B_P(t) = \frac{B_{P0}}{1 + \left(\frac{t}{\tau \cdot q}\right)^q}, \quad (3)$$

where $\tau$ is a time constant of the decay, q is a dimensionless decay rate parameter, and $B_{P0}$ is a value of $B_P$ at time t=0. Decay shapes are illustrated in FIG. 5 for $\tau=5$ μs and q=0.5, 1, and 2. For the decay shape with q=1 presented in FIG. 5, the adiabacity factor can be represented as $$\xi = \frac{|\vec{\Omega}|}{\gamma \cdot |\vec{B}|} \propto \frac{1}{B_{P0}}. \quad (4)$$

From equation (4), the adiabacity factor is proportional to $1/B_{P0}$. Thus, excitation will move toward more adiabatic for stronger polarizing magnetic fields that are expected in the shallow regions. Therefore, the NMR signals derived from the magnetization changes in the shallow regions will not be significant. Excitation of the nuclei at a selected distance from the logging instrument 10 is discussed in detail next.

Figure 6:
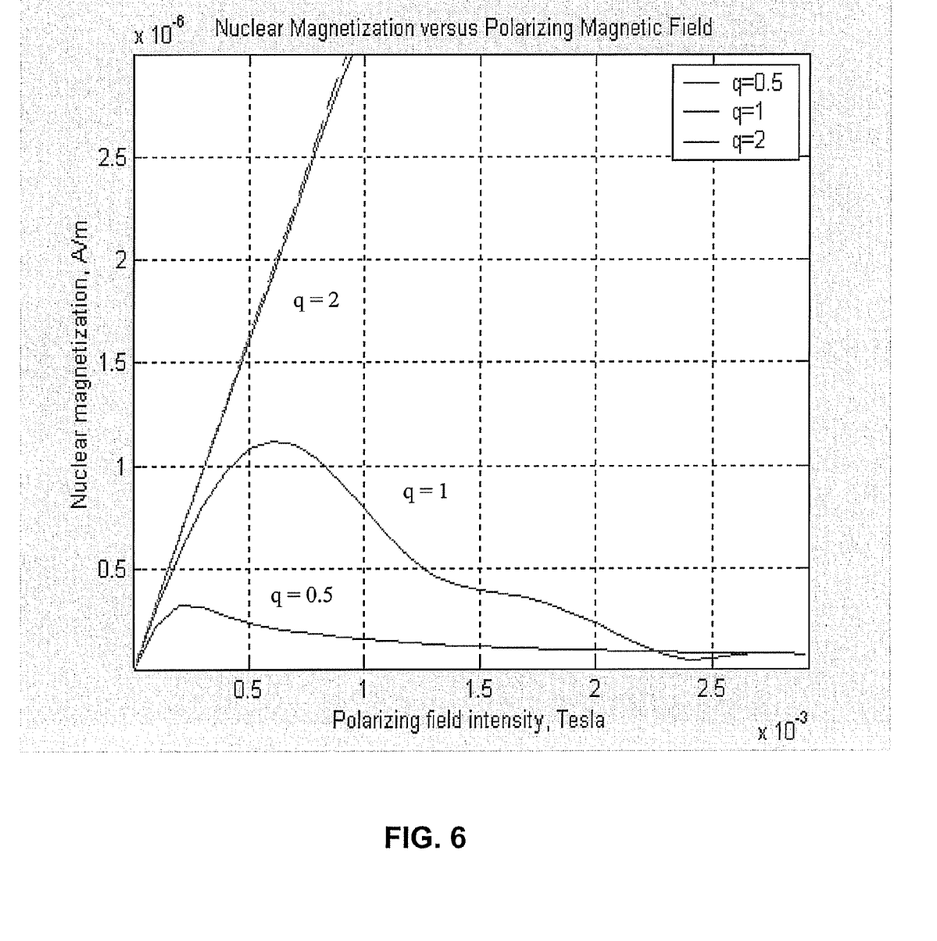
FIG. 6 illustrates an example a graph of a solution to a Bloch equation for a magnitude of oscillating nuclear magnetization as a function of strength of the polarizing magnetic field.

The Bloch equation (1) may be solved to determine a magnitude of oscillating nuclear magnetization resulting from a decaying polarizing magnetic field. Equation (3) may be used to determine the decay shape of the decaying polarizing magnetic field. The oscillating nuclear magnetization is related to the NMR signal induced in the receiver coil 2. FIG. 6 illustrates an example of graphs of solutions to the Bloch equation (1) for the magnitude of oscillating nuclear magnetization as a function of strength of the polarizing magnetic field for different decay shapes. One may notice a pronounced maximum of the magnitude of the oscillating nuclear magnetization for the decay shape related to q=1. The pronounced maximum indicates selective excitation of the nuclei by decay of the polarizing magnetic field. The selective excitation may provide for spatial selective excitation in cases where the polarizing magnetic field exhibits spatial dependence. In the above example, the decay shape related to q=1 provides an optimal decay shape for spatial selective excitation.

Figure 7:
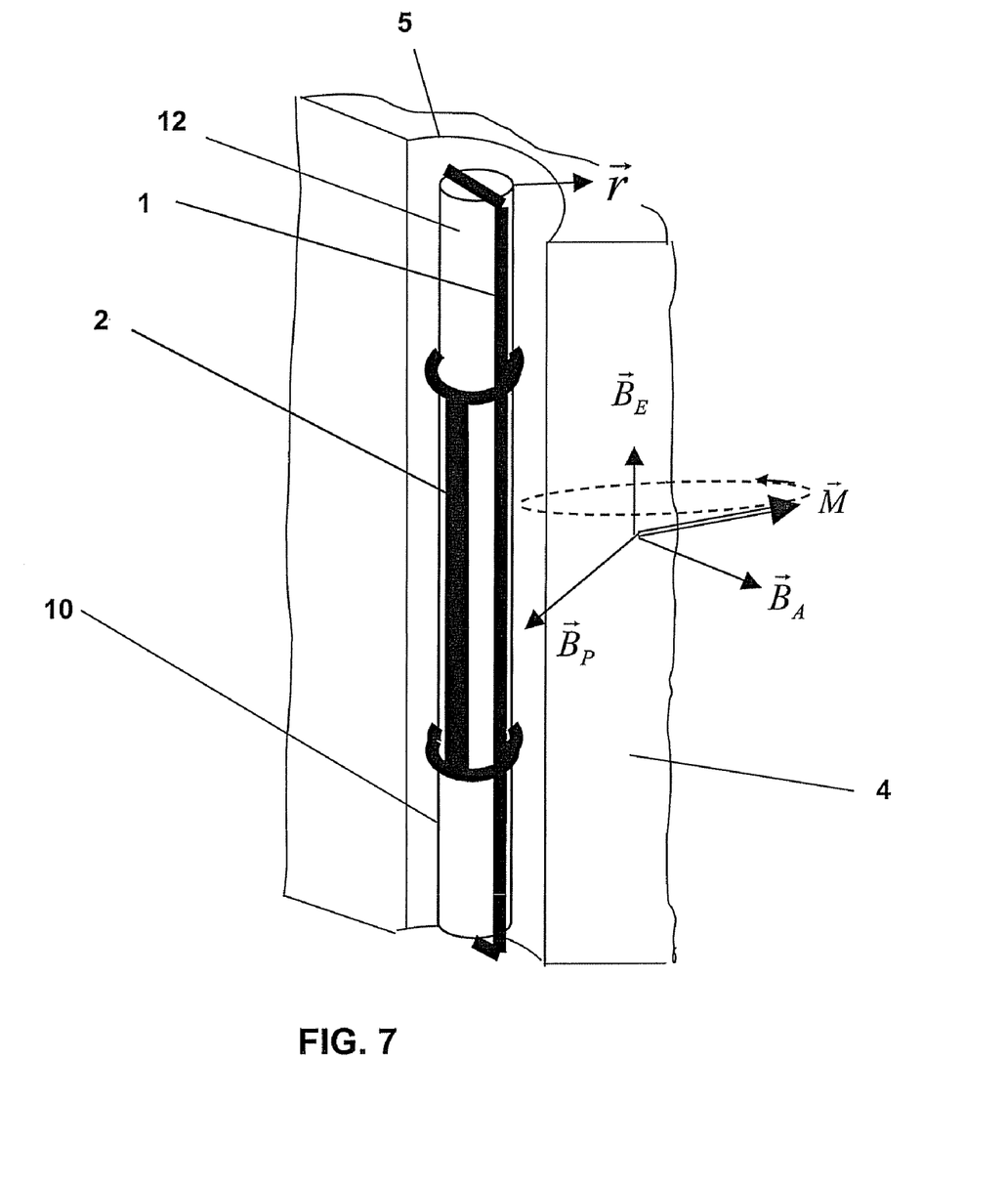
FIG. 7 illustrates an exemplary embodiment of a logging instrument for performing earth's magnetic field NMR measurements in a borehole.

FIG. 7 illustrates an exemplary embodiment of the well logging instrument 10 for implementing the teachings herein. The well logging instrument 10 is placed in the borehole 5 traversing the formation 4. The polarizing coil 1 is placed on a coil framer 12 that may or may not contain a ferromagnetic core. The polarizing coil 1 provides a switchable source of the polarizing magnetic field. The receiver coil 2 is wound in a plane perpendicular to the plane of the polarizing coil 1. A direction of the polarizing magnetic field $\vec{B}_P$, a receiver coil sensitivity $\vec{B}_A$, and the earth's magnetic field $\vec{B}_E$ are displayed in FIG. 7. Also displayed in FIG. 7 is precession of nuclear magnetization $\vec{M}$ at a radius r from the polarizing coil 1. The precession results in an oscillating magnetic field $\vec{B}_S$ at the receiver coil 2.

Figure 8:
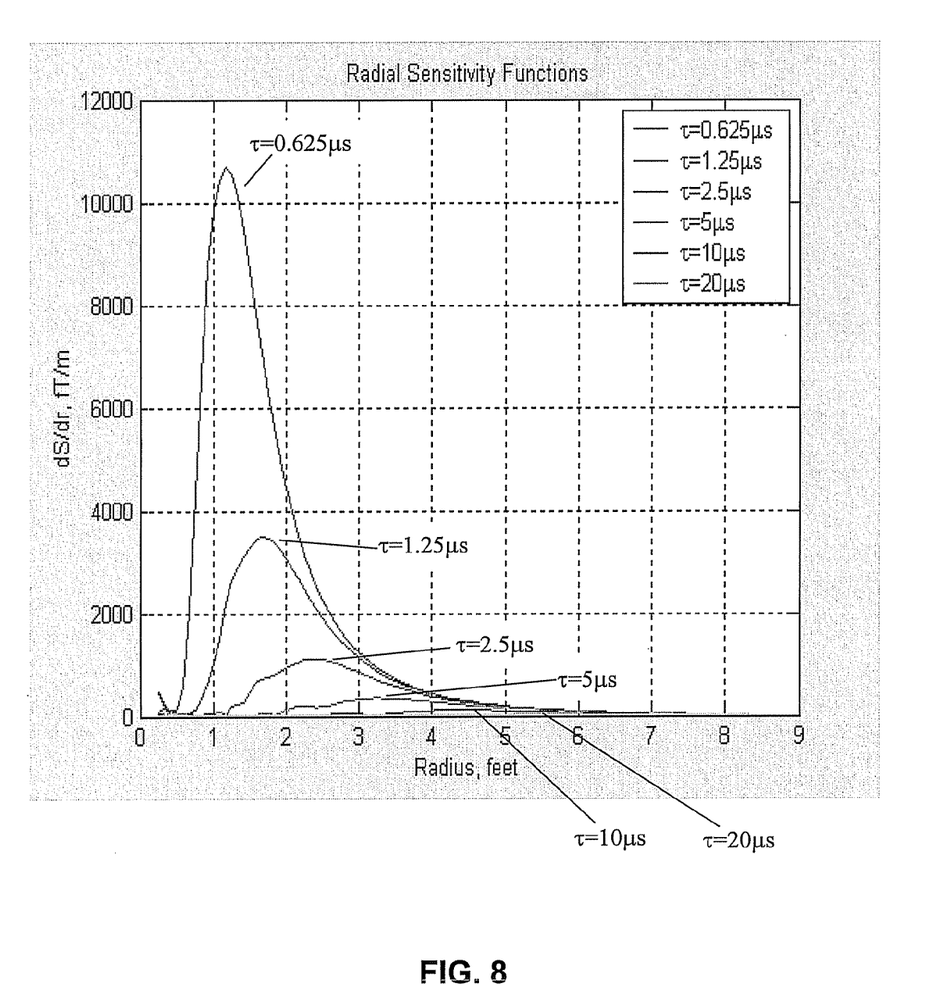
FIG. 8 illustrates an example of a sensitivity distribution as a function of a radius of a cylindrical shell.

In order to determine a magnitude of the oscillating magnetic field $\vec{B}_S$, a sensitivity distribution of a signal coming from the precession of nuclear magnetization $\vec{M}$ on the cylindrical shell dr at radius r is modeled. FIG. 8 illustrates an example of the sensitivity distribution. Denoted S is the magnitude of the magnetic field $\vec{B}_S$. The sensitivity distribution dS/dr was modeled for a number of different time constants $\tau$: $\tau=0.625$ μs, $\tau=1.25$, $\tau=2.5$ μs, $\tau=5$ μs, $\tau=10$ μs, and $\tau=20$ μs. As illustrated in FIG. 8, a depth of investigation can be controlled by selecting an appropriate time constant for the decay shape of the polarizing magnetic field. The values of S correspond to using the polarizing coil 1 that is three meters long having a dipole moment of 7,500 A·m².

Figure 9:
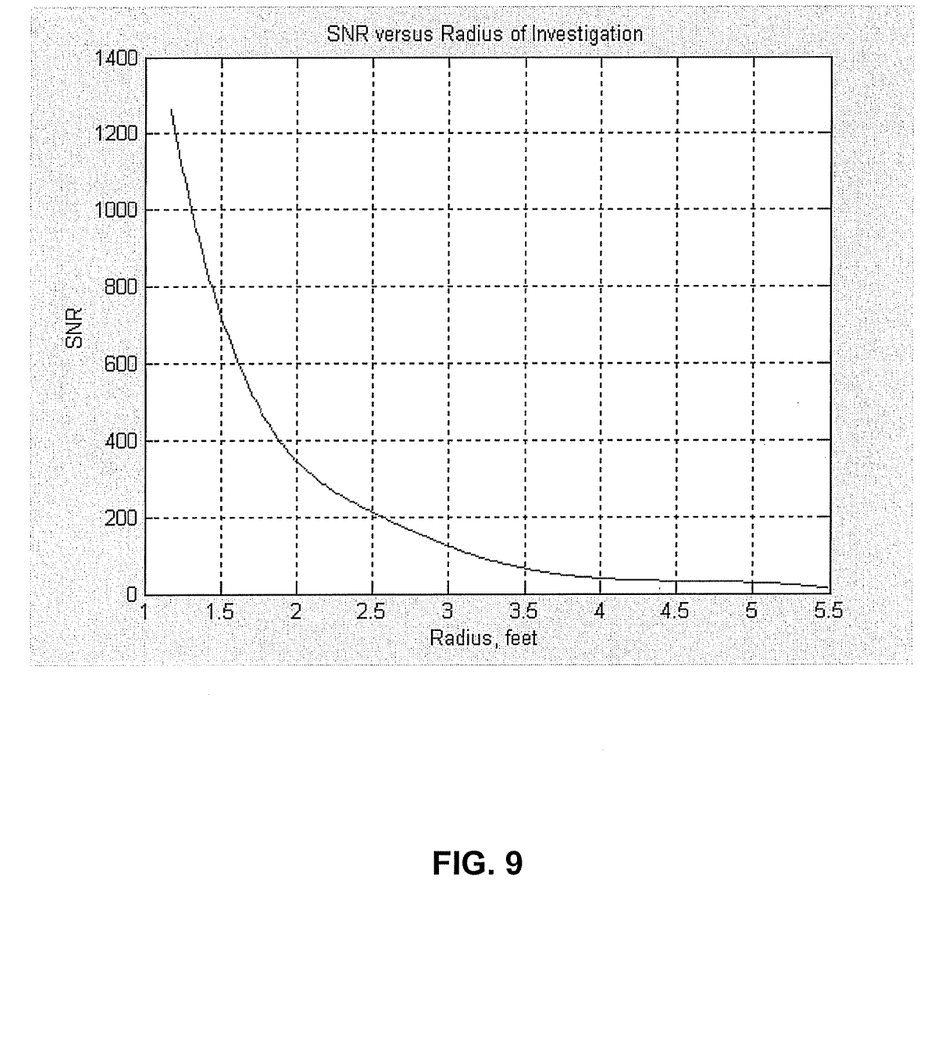
FIG. 9 illustrates an example of a graph of SNR as a function of radius corresponding to a maximum sensitivity.

FIG. 9 illustrates an example of signal-to-noise ratio (SNR) as a function of radius (radius of investigation or, approximately, depth of investigation) corresponding to a maximum sensitivity on the sensitivity distribution presented in FIG. 8. The SNR is calculated for the dipole moment 7,500 A·m² and noise density $N_r$ of the receiver coil 2 where $N_r$=0.2 fT/$\sqrt{Hz}$ (0.2 femtoTesla per square root of Hertz) in the bandwidth $\Delta f$=400 Hz. High potential SNR suggests that nuclei having a much smaller signal than hydrogen nuclei can be detected. For example, an amount of carbon in a specified volume surrounding the borehole 5 can be assessed. The magnetic field $\vec{B}_S$ at the receiver coil 2 produced by precession of carbon nuclei will be about 1,500 times lower that of the hydrogen nuclei. Narrowing the bandwidth to about 50 Hz with the SNR at about 1500 will result in the SNR being approximately three per one free induction decay (FID). Stacking multi-FID data provides a sufficient SNR for assessing carbon volume density in the formation 4. Other nuclei that can be detected and quantified include sodium nuclei. The sodium nuclei can produce a higher SNR than the SNR produced by the carbon nuclei.

Figure 10:
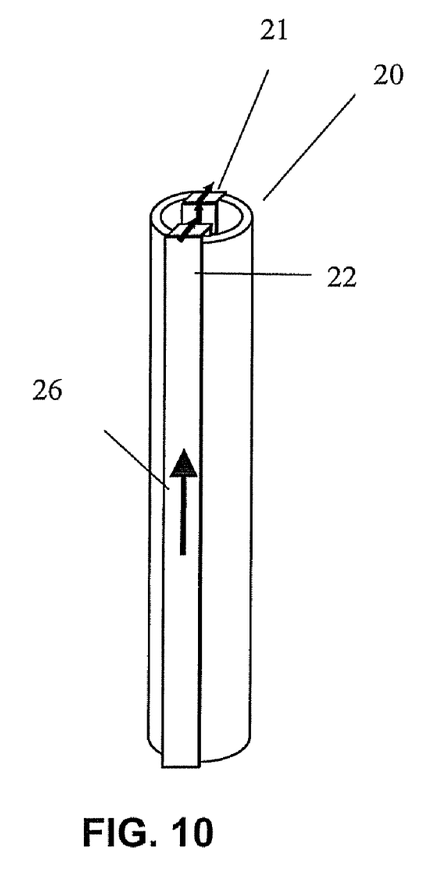
FIG. 10 illustrates an exemplary embodiment of a fast switchable source of the polarizing magnetic field.
Figure 11:
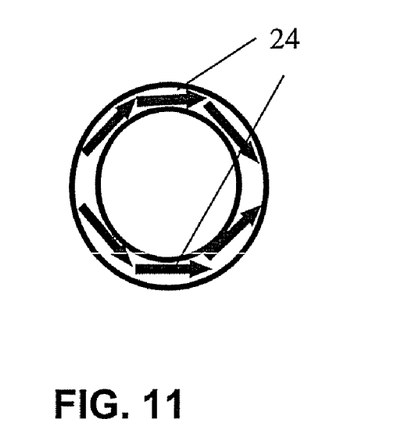
FIG. 11 illustrates an exemplary embodiment of a cross-section of a magnetic core showing a direction of magnetization.
Figure 12:
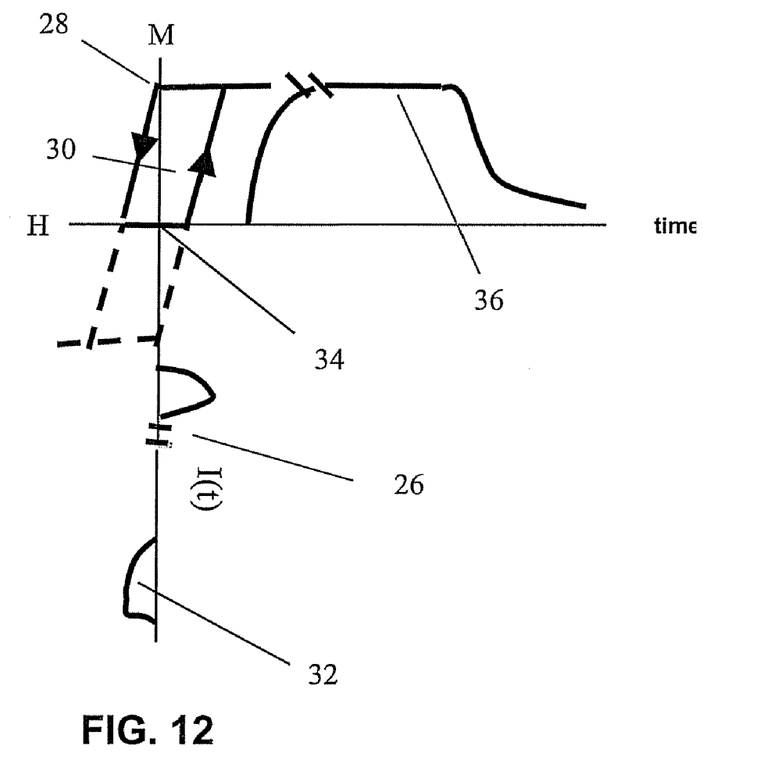
FIG. 12 illustrates examples of graphs of residual magnetization, pulses of current and the polarizing magnetic field.

FIGS. 10, 11 and 12 illustrate an exemplary embodiment of a fast switchable source of the polarizing magnetic field. The fast switchable source uses electric current conducted through windings to produce the polarizing magnetic field. Referring to FIG. 10, the fast switchable source includes a first winding 21 and a second winding 22 disposed on opposite sides of a magnetic core 20. The magnetic core 20 has a hollow cylindrical shape. The first winding 21 and the second winding 22 may have a small number of turns (in some cases only one turn each) in order to have low inductance. In general, the low inductance is a requirement for fast switching.

The fast switchable source operates as follows. Referring to FIGS. 10 and 12, a first pulse of current 26 is applied to the first winding 21 and the second winding 22 (referred to as windings 21 and 22). The first pulse of current 26 is applied in directions in the windings 21 and 22 such as to create magnetization in the core 20 in a transversal direction. The magnetization in the magnetic core 20 in a transversal direction creates a transversal dipole. A top view of a cross-section of the magnetic core 20 showing magnetization 24 of the magnetic core 20 is illustrated in FIG. 11. Magnetic material of the magnetic core 20 may have substantial hysteresis that results in residual magnetization remaining after the first pulse of current 26 is turned off. A magnetization cycle corresponding to switching the transversal dipole "on" and "off" is illustrated with respect to a hysteresis cycle 30 in FIG. 12. Referring to FIG. 12, after the first pulse of current 26 is turned off, a magnetization state corresponds to residual magnetization 28 on the hysteresis cycle 30. No current is required in windings 21 and 22 to maintain magnetization of the magnetic core 20. Consequently, no current in the windings 21 and 22 is required to maintain the polarizing magnetic field generated by the transversal dipole. Because DC current is not required to maintain the polarizing magnetic field, DC power loss does not occur in the windings 21 and 22. Thus, efficiency of the source of the polarizing magnetic field increases. The residual magnetization 28 makes the transversal dipole effective at generating a 2,500 A·m² magnetic dipole per meter length. DC power consumption of the source of the polarizing magnetic field is about 200 W for four seconds of a magnetization-demagnetization cycle. Referring to FIG. 12, the second pulse of current 32 causes demagnetization of the magnetic core 20 resulting in removal of the polarizing magnetic field according to a selected decay shape. A trailing edge of the second pulse of current 32 is optimized in order to provide the decay shape to facilitate the spatial selective excitation discussed above. The removal of the polarizing field according to the decay shape results in precession of nuclear spins in a selected region (also referred to as an investigation region). Referring to FIG. 12, a time dependent polarizing magnetic field 36 is illustrated.

Figure 13:
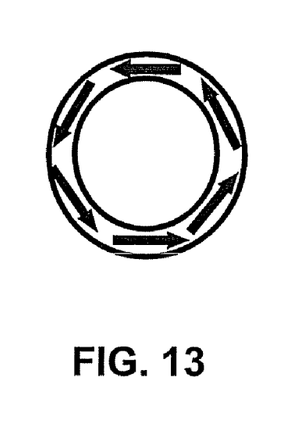
FIG. 13 illustrates an exemplary embodiment of the cross-section of the magnetic core showing no magnetic poles.

A zero net magnetization state 34 of the magnetic core 20 is depicted in FIG. 12. The zero net magnetization state 34 may be realized in different ways. One way is to set an amplitude of the second pulse of current 32 corresponding to a magnetic field close to a coercive force of the magnetic core 20 derived from the hysteresis cycle 30 in FIG. 12. Another way is to apply a saturating pulsed current with a polarity opposite of the first pulse of current 26 to only one of the first winding 21 and the second winding 22. The top view of the cross-section of the magnetic core 20 showing the magnetization direction corresponding to the saturating pulsed current is illustrated in FIG. 13. Referring to FIG. 13, arrows showing the magnetization direction represent a "no-magnetic poles" structure with little or no polarizing magnetic field generated in the formation 4.

Some residual polarizing magnetic field may remain after demagnetization of the magnetic core 20. In one exemplary embodiment, the residual polarizing magnetic field can be reduced or eliminated by using a thin magnetic shield place on a surface of the magnetic core 20. The thin magnetic shield will be saturated in the "on" state of the magnetic core 20. The thin magnetic shield, when saturated, will not produce any significant reduction of the polarizing magnetic field produced by the transversal dipole. When the magnetic core 20 is in the "off" state, the thin magnetic shield will "short-circuit" any magnetic field produced by the transversal dipole.

Distortions of the earth's magnetic field due to magnetizing the magnetic core 20 in the earth's magnetic field may affect the NMR signals. In one exemplary embodiment, the distortions may be reduced or eliminated by employing a set of coils with adjustable current. The coils may be used to counteract the distortions.

Typically, the well logging instrument 10 includes adaptations as may be necessary to provide for operation during drilling or after a drilling process has been undertaken.

Figure 14:
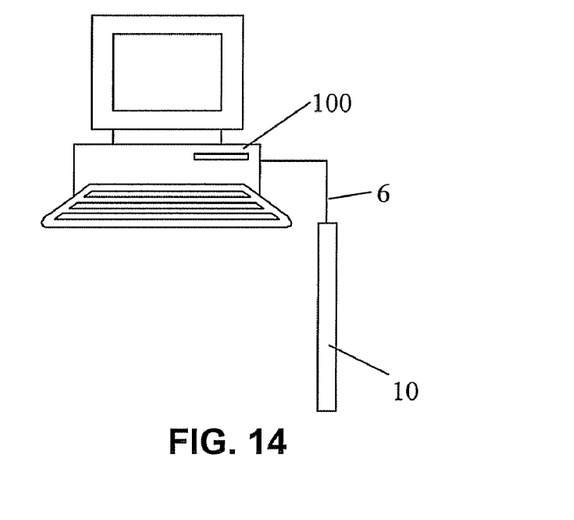
FIG. 14 illustrates an exemplary embodiment of a computer coupled to the logging instrument.

Referring to FIG. 14, an apparatus for implementing the teachings herein is depicted. In FIG. 14, the apparatus includes a computer 100 coupled to the well logging instrument 10. Typically, the computer 100 includes components as necessary to provide for the real time processing of data from the well logging instrument 10. Exemplary components include, without limitation, at least one processor, storage, memory, input devices, output devices and the like. As these components are known to those skilled in the art, these are neither depicted in any detail nor discussed further herein.

Typically, the teachings herein are reduced to an algorithm that is stored on machine-readable media. The algorithm is implemented by the computer 100 and provides operators with desired output. The output is typically generated on a real-time basis.

As used herein generation of data in "real-time" is taken to mean generation of data at a rate that is useful or adequate for making decisions during or concurrent with processes such as production, experimentation, verification, and other types of surveys or uses as may be opted for by a user or operator. As a non-limiting example, real-time measurements and calculations may provide users with information necessary to make desired adjustments during the drilling process. In one embodiment, adjustments are enabled on a continuous basis (at the rate of drilling), while in another embodiment, adjustments may require periodic cessation of drilling for assessment of data. Accordingly, it should be recognized that "real-time" is to be taken in context, and does not necessarily indicate the instantaneous determination of data, or make any other suggestions about the temporal frequency of data collection and determination.

A high degree of quality control over the data may be realized during implementation of the teachings herein. For example, quality control may be achieved through known techniques of iterative processing and data comparison. Accordingly, it is contemplated that additional correction factors and other aspects for real-time processing may be used. Advantageously, the user may apply a desired quality control tolerance to the data, and thus draw a balance between rapidity of determination of the data and a degree of quality in the data.

Figure 15:
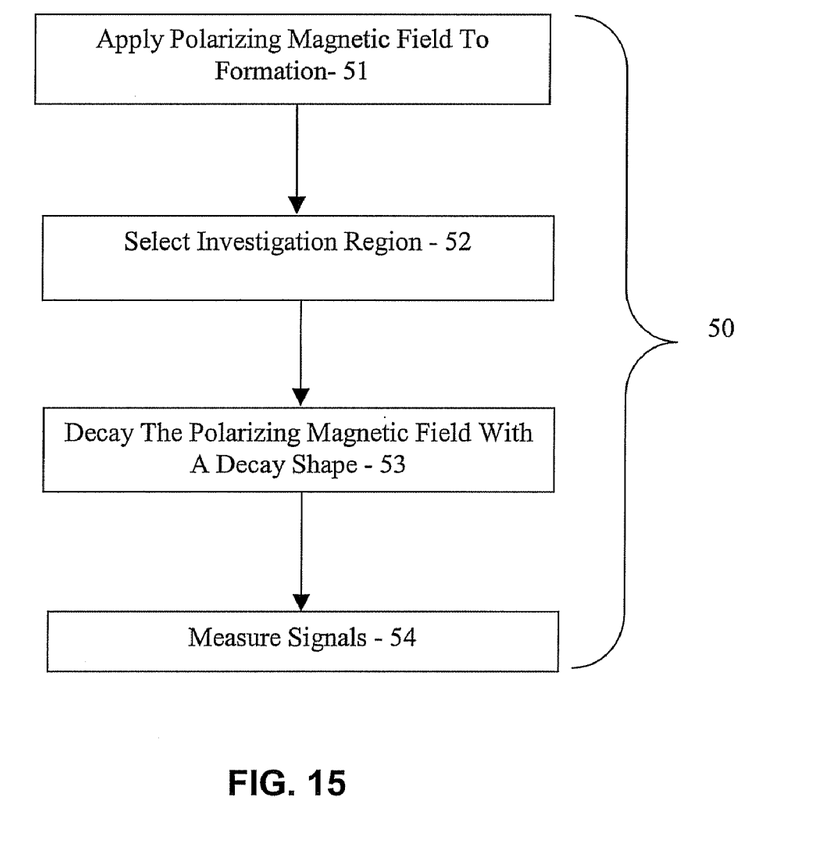
FIG. 15 illustrates an exemplary method for using NMR to measure characteristics of a formation at a selected distance from the logging instrument.

FIG. 15 presents an exemplary method 50 for measuring a property of the formation 4 at a selected distance from the borehole 5. A first step 51 calls for applying a polarizing magnetic field 36 to the formation 4. In general, the first step 51 includes applying the polarizing magnetic field 36 having a spatially inhomogeneous magnitude. A second step 52 calls for selecting an investigation region in the formation 4. A third step 53 calls for decaying the polarizing magnetic field according to a decay shape that will substantially excite only nuclei in the investigation region. A fourth step 54 calls for measuring signals induced by precession of the nuclei in the investigation region.

Figure 16:
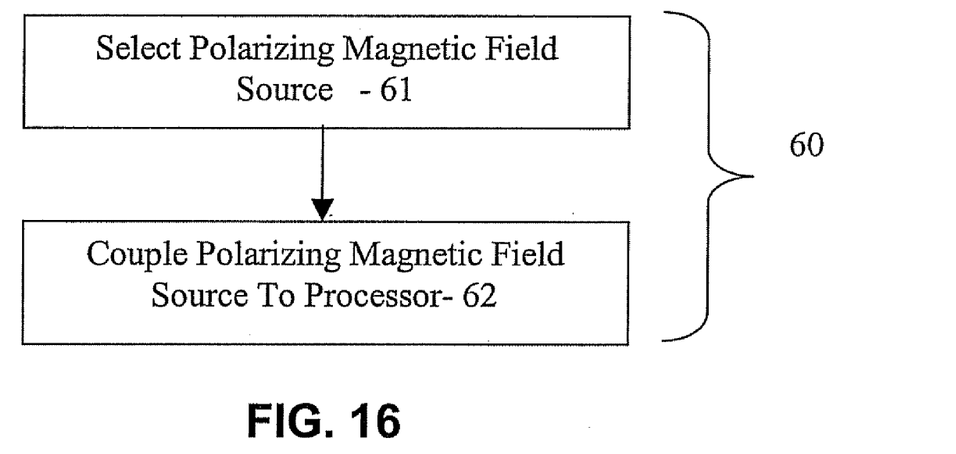
FIG. 16 illustrates an exemplary method for producing the logging instrument.

FIG. 16 presents an exemplary method 60 for producing the well logging instrument 10. A first step 61 calls for selecting a polarizing magnetic field source. Typically, the polarizing magnetic field source includes a dipole. The dipole may include the magnetic core 20 with the first winding 21 and the second winding 22. The magnetic core 20 may have a hollow cylindrical shape. A second step 62 calls for coupling the polarizing magnetic field source to a processor. In general, the processor provides instructions for decaying the polarizing magnetic field.

Figure 17:
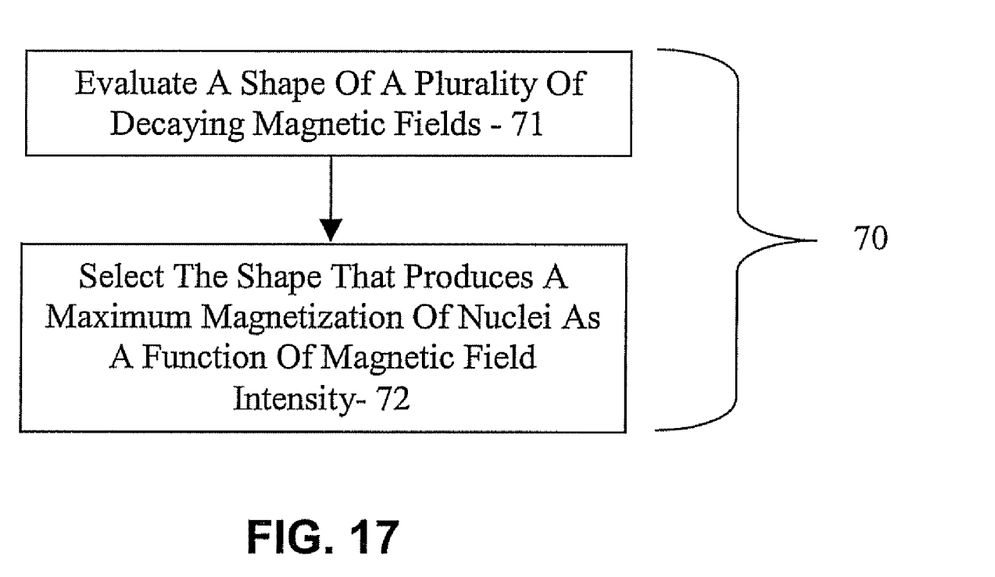
FIG. 17 illustrates an exemplary method for selecting a decay shape.

FIG. 17 presents an exemplary method 70 for selecting a decay shape. A first step 71 calls for evaluating a shape of a plurality of decaying magnetic fields. The first step 71 may also include solving the Bloch equation for various shapes to derive magnetization as a function of polarizing field intensity for each shape. A second step 72 calls for selecting the shape that produces a maximum magnetization of nuclei as a function of magnetic field intensity to provide the decay shape. The method 70 may also include correlating the maximum excitation to an investigation region. The investigation region is typically beyond the shallow region. Typically, nuclei in the investigation region receive the maximum magnetization resulting in the nuclei producing a maximum precession amplitude. Generally, the maximum precession amplitude results in strong signals compared to signals from nuclei in other regions. In one embodiment, the method 70 may include calculating a signal induced in the receiver coil 2 by precession of nuclei as a function of distance from the coil for various values of the time constant. Finally, the method 70 may include at least one of evaluating and selecting equation (3) as the shape with q=1.

In support of the teachings herein, various analysis components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a sample line, sample storage, sample chamber, sample exhaust, pump, piston, power supply (e.g., at least one of a generator, a remote supply and a battery), vacuum supply, pressure supply, refrigeration (i.e., cooling) unit or supply, heating component, motive force (such as a translational force, propulsional force or a rotational force), magnet, electromagnet, sensor, electrode, transmitter, receiver, transceiver, controller, optical unit, electrical unit or electromechanical unit may be included in support of the various aspects discussed herein or in support of other functions beyond this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A downhole nuclear magnetic resonance method for measuring a property of a formation, the method comprising:
applying a polarizing magnetic field to the formation, the field comprising a spatial distribution of magnitude;
selecting an investigation region of the formation;
decaying the polarizing magnetic field according to a decay shape to provide for substantially exciting only nuclei in the investigation region; and
measuring signals induced by precession of the nuclei in the investigation region.

2. The method as in claim 1, wherein selecting comprises selecting the investigation region according to a desired depth from an edge of the borehole.

3. The method as in claim 2, wherein the desired depth exceeds about three inches.

4. The method as in claim 1, wherein decaying comprises applying a pulse of current, the current comprising an amplitude corresponding to a magnetic field close to a coercive force of a magnetic core and a polarity that corresponds to opposing the polarizing magnetic field.

5. The method as in claim 1, wherein decaying comprises applying a pulse of current, the current comprising an amplitude to drive a magnetic core into saturation and a polarity that opposes formation of a dipole in the core.

6. The method as in claim 1, further comprising counteracting distortions in the earth's magnetic field due to magnetizing a magnetic core in a magnetic dipole, the counteracting comprising adjusting current in a coil.

7. A method for selecting a decay shape for decaying a polarizing magnetic field in nuclear magnetic resonance measurements, the method comprising:
evaluating a shape of a plurality of decaying magnetic fields; and
selecting the shape that produces a maximum magnetization of nuclei as a function of magnetic field intensity to provide the decay shape.

8. The method as in claim 7, wherein the maximum magnetization is greater than a magnetization immediately preceding and following the maximum magnetization.

9. The method as in claim 7, further comprising solving a Bloch equation with the shape as input to determine the maximum magnetization of the nuclei as a function of magnetic field intensity.

10. The method as in claim 7, further comprising correlating the maximum magnetization to an investigation region of a formation.

11. The method as in claim 10, wherein correlating comprises determining a signal induced in a receiver coil by precession of the nuclei as a function of distance from the coil, the precession resulting from decaying the polarizing magnetic field according to the decay shape.

12. The method as in claim 10, further comprising selecting the investigation region comprising the distance at which the signal is a maximum, wherein the signal immediately preceding and following the maximum is less than the maximum.

13. The method as in claim 7, further comprising the shape $$B_P(t) = \frac{B_{P0}}{1 + \left(\frac{t}{\tau \cdot q}\right)^q}$$

where $\tau$ represents a time constant of the shape, q represents a dimensionless decay rate parameter, and $B_{P0}$ is a magnitude of the polarizing magnetic field at time t=0.

14. The method as in claim 13, further comprising q=1.

15. A nuclear magnetic resonance instrument for measuring a property of a formation downhole, the instrument comprising:
a source adapted for applying a polarizing magnitude field to the formation and decaying the polarizing magnetic field according to a decay shape to provide a maximum precession amplitude of nuclei in an investigation region beyond a shallow region.

16. The instrument as in claim 15, wherein the source comprises a magnetic dipole.

17. The instrument as in claim 16, wherein the dipole comprises:
a hollow cylindrical magnetic core; and
two sets of windings, the two sets of windings disposed approximately 180 degrees apart on the circumference of the core.

18. The instrument as in claim 15, wherein the device comprises a processor.

19. The instrument as in claim 15, further comprising a coil, the coil comprising a coupling for coupling to an adjustable source of current, the coil providing the current to counteract distortions to earth's magnetic field due to magnetization of a magnetic core.

20. The instrument as in claim 15, further comprising a thin magnetic shield exterior to the source.

21. A method for producing an instrument for measuring a property of a formation downhole, the method comprising:
selecting a source of a polarizing magnetic field; and
coupling the source to a processor, the processor comprising instructions for decaying the field according to a decay shape to provide a maximum precession amplitude of nuclei in an investigation region beyond a shallow region.

22. The method as in claim 21, further comprising selecting a thin magnetic shield and placing the shield exterior to the dipole.

23. The method as in claim 21, further comprising selecting a coil for conducting an adjustable current, the current for counteracting distortions in the earth's magnetic field due to magnetizing a magnetic core; and coupling the coil to the a source of current.

* * * * *